(12) United States Patent
Viola et al.

(10) Patent No.: US 8,946,271 B2
(45) Date of Patent: Feb. 3, 2015

(54) WATER SOLUBLE FUROXAN DERIVATIVES HAVING ANTITUMOR ACTIVITY

(75) Inventors: Antonella Viola, Milan (IT); Enzo Bronte, Padua (IT); Marco Crosetti, Milan (IT); Loretta Lazzarato, Milan (IT); Roberta Fruttero, Milan (IT); Alberto Gasco, Milan (IT)

(73) Assignees: Humanitas Mirasole S.p.A., Rozzano (MI) (IT); Istituto Oncologico Veneto IRCCS, Padua (IT)

(*) Notice: Subject to any disclaimer, the term of this patent is extended or adjusted under 35 U.S.C. 154(b) by 223 days.

(21) Appl. No.: 13/522,026

(22) PCT Filed: Feb. 23, 2011

(86) PCT No.: PCT/IB2011/050743
§ 371 (c)(1),
(2), (4) Date: Oct. 24, 2012

(87) PCT Pub. No.: WO2011/104671
PCT Pub. Date: Sep. 1, 2011

(65) Prior Publication Data
US 2013/0035360 A1   Feb. 7, 2013

(30) Foreign Application Priority Data
Feb. 23, 2010   (IT) ............... MI2010A0287

(51) Int. Cl.
*C07D 271/08* (2006.01)
*A61K 31/4245* (2006.01)

(52) U.S. Cl.
CPC .......... *C07D 271/08* (2013.01); *A61K 31/4245* (2013.01)
USPC .......................................... 514/364; 548/125

(58) Field of Classification Search
CPC .......................... C07D 271/08; A61K 31/4245
USPC .......................................... 514/364; 548/125
See application file for complete search history.

(56) References Cited

U.S. PATENT DOCUMENTS
2008/0293781 A1 * 11/2008 Gasco et al. ................. 514/361

FOREIGN PATENT DOCUMENTS
WO   2010081488 A1   7/2010

OTHER PUBLICATIONS

Turnbull et al. British Journal of Pharmacology 2006, 148, 517-526.*
Clara Cena, Marco L.Lolli, Loretta Lazzarato, Elena Guaita, Giuseppina Morini, Gabriella Coruzzi, Stuart P. McElroy, Ian L. Megson, Roberta Fruttero and Alberto Gasco, Antiinflammatory, Gastrosparing, and Antiplatelet Properties of New No-Donor Esters of Aspirin, Journal of Medicinal Chemistry, 2003, pp. 747-754, vol. 46, No. 5, American Chemical Society, Washington, DOI: 1021/JM020969T.
Claudio Medana, Antonella Di Stilo, Sonja Visentin, Roberta Fruttero, Alberto Gasco, Dario Ghigo and Amalia Bosia, No Donor and Biological Properties of Different Benzofuroxans, Pharmaceutical Research, Kluwer Academic Publishers, Jun. 1, 1999, pp. 956-960, vol. 16, No. 6, Plenum Publishing Corporation, New York, DOI: 10.1023/A: 1018974409622.
Database Beilstein (online), Beilstein Institute for Organic Chemistry, Frankfurt-Main, DE; 1931, Frejka et al.: XP002600024, Database accession No. 3178253.

* cited by examiner

*Primary Examiner* — Joseph Kosack
*Assistant Examiner* — Matthew Coughlin
(74) *Attorney, Agent, or Firm* — Robert E. Alderson Jr.

(57) ABSTRACT

Water soluble compounds having a furoxan structure which are capable of inhibiting metabolic pathways involved in the development of the tumours are provided. The use of such compounds as a medicament in the therapy of the tumours and as an adjuvant in the immunotherapy protocols against neoplasms is also described.

8 Claims, 8 Drawing Sheets

WATER SOLUBLE FUROXAN DERIVATIVES HAVING ANTITUMOR ACTIVITY

CROSS-REFERENCE TO RELATED APPLICATIONS

This application is a National Phase Application of PCT International Application No. PCT/IB2011/050743, International Filing Date, 23 Feb. 2011, claiming priority to Italian Patent Application No. MI2010A000287, filed 23 Feb. 2010.

FIELD OF THE INVENTION

The present invention finds application in the field of medicine and, in particular, it regards novel water soluble compounds with furoxan structure capable of inhibiting metabolic pathways involved in the development of the tumours.

BACKGROUND OF THE INVENTION

Prostate cancer is the second cause of death in the male population of the western countries. In case of localised cancer, radical prostatectomy and the local radiotherapy have revealed to be efficient while in the case of metastatic prostate carcinoma (PCa), they have unfortunately revealed poor curing properties.

Thus, it is necessary to find alternative therapies for the metastatic prostate cancer refractory to hormone treatments. The success of such approach depends on the ability of the cytotoxic T cells to eliminate the tumour cells. However, should the tumour environment exert a suppressive action on the action of the antigen-specific tumour-infiltrating lymphocytes (TIL), the immunotherapy has poor success.

Thus, understanding the biology of the TIL cells and the modulation of the response thereof by the tumour is of fundamental importance.

The role of the prostatic tumour environment in the modulation of the response of the T cells was analysed by using culture of human PCa on a collagen matrix. This technique offers the advantage of maintaining the microenvironment intact, as well as all the factors that can influence the activity of the TIL cells, such as the cell-cell interaction or interaction between a cell attached to the matrix and the interstitial fluid. This new approach has allowed to obtain considerable results. Generally, the TIL in the PCa samples are mainly differentiated T CD8+ (CD8+, CF45RA+, CD62L− and CCR7−) and perforin positive lymphocytes, and thus potentially capable of eliminating the cancerous cells. However, the latter are in dormant state, given that they do not express activation markers as CD25, CD69 and CD137. Furthermore, contrary to the lymphocytes present in non-tumour prostate tissues and in the peripheral blood, the TILs have no response to activation signals which act either on the TCR or downstream signal pathways, indicating a deficiency restricted to the tumour. Additionally, there has been extensive evidence that the arginase enzymes (ARG) and NO-synthase (NOS) are overexpressed in PCa if compared to the hyperplasic prostate, with the interesting observation revealing that actually the tumour cells and not the infiltrating myeloid cells, could be the main source of enzymes. The results indicate that the steady-state regulation of the dormant state of the TIL depends on the increased intratumoral metabolism of the L-arginine amino acid (L-Arg), given that the simple addition of specific ARGs and NOS inhibitor was sufficient to arouse the CTLs, activate them and start a series of events that lead to the cytolytic polarisation of the granules and to the elimination of the target. In addition, it was also demonstrated that the presence of high levels of nitrotyrosine in the TIL, which suggests of the local production of peroxynitrite, is possibly due to the activity of ARG and NOS, given that inhibiting the activity of the enzymes also lead to reduced tyrosine nitration.

These results identify a mechanism through which the human prostate cancer induces immunosuppression in situ. Therefore, active ingredients that control the generation of reactive nitrogen species (RNS) could be useful in the immunotherapeutic approach for the treatment of the cancer, creating a tumour environment favourable for the activation of the lymphocytes (Bronte et al., 2005).

The results of the clinical assays revealed that the efficiency of the different immunotherapeutic approaches is not suitable for an immediate and extensive transfer to the therapeutic treatment on patients.

An important emerging concept is that the altered metabolism present in the tumour microenvironment can have a deep impact on the anti-tumour activity. Considering the previously mentioned results, it is clear that the active ingredients that control the generation of the reactive nitrogen species (RNS) can considerably increase the impact of the immunotherapeutic approaches for the treatment of cancer.

Already known conventional adjuvants, such as the cytokines and activators of the antigen presenting the cells, are characterised by an extensive activity on the immune system, but they lack selectivity and can lead to considerable adverse effects.

Hence, there continuously arises the need of finding novel compounds free of such drawbacks.

SUMMARY OF THE INVENTION

Thus, it is the purpose of the present invention to provide novel compounds which are capable of interfering with some metabolic pathways correlated to the development of tumours and which enhance the function of the antitumor lymphocytes present spontaneously, generated in the patient after vaccination or transferred after cellular therapy (ACT). A first object of the invention regards water soluble 1,2,5-oxadiazole N-oxide derivatives according to the attached claims.

In particular, the invention regards the specific compounds of formula (II), (III) and (IV).

In a second object, the invention describes the compounds of the invention for use as a medicament and, in a preferred aspect, for use as a medicament in the therapy of pathologies characterised by the generation of reactive nitrogen species.

According to an even more preferred aspect, such pathologies comprise neoplasms, inflammatory diseases or chronic infections.

The compounds are described in particular for use in the treatment of the prostate cancer.

In a further object, the compounds described in the invention are used as adjuvants in the immunotherapy protocols against cancer.

Furthermore, pharmaceutical compositions comprising one or more compounds according to the invention are described.

DETAILED DESCRIPTION OF THE INVENTION

Figure 1:
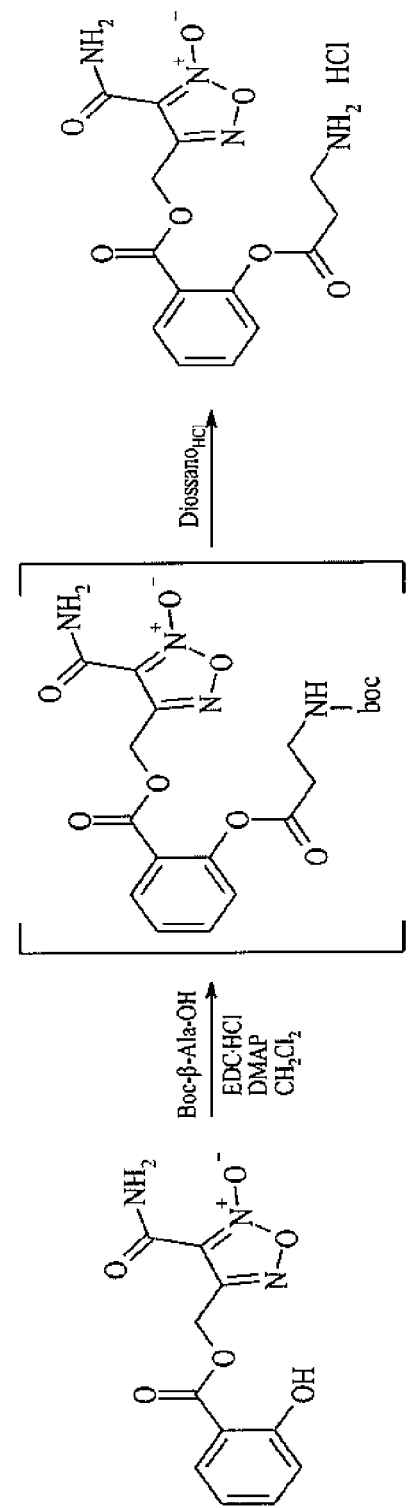
FIG. 1 represents the synthesis scheme of the compound MC526.

According to a first object, the invention regards the soluble 1,2,5-oxadiazole N-oxide derivatives of general formula (I):

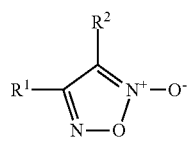

(I)

wherein $R^1$ can be a linear or branched saturated C1-C8 alkyl or a linear or branched C2-C8 hydrocarbon chain comprising one or more unsaturated bonds, substituted with one or more acyloxy groups (—O—C(O)—$R^3$), wherein $R^3$ is an arylic group Ar substituted in any free position with one or more acyloxy groups (—O—C(O)—$R^4$), wherein $R^4$ is a linear or branched saturated C1-C8 alkyl possibly substituted with one or more groups (—OH), (—SH), (—COO$R^5$), (—N$R^5_2$) wherein $R^5$ is independently selected from among H and $R^4$, or $R^1$ can be such that the group Ar or $R^1$ and $R^2$ together with the atoms to which they are bound form a [1,2,5]oxadiazole [3,4-e][2,1,3]benzoxadiazole 3,6-N-dioxide, and wherein $R^2$ can be a cyan group (—CN) or an amide group (—CON$R^5_2$), wherein each $R^5$ is independently H or $R^4$; and pharmaceutically acceptable salts thereof.

For the purposes of the present invention, a saturated C1-C8 alkyl comprises methyl, ethyl and, in the linear or branched forms, propyl, butyl, pentyl, hexyle, heptyl, octyl.

The expression C2-C8 hydrocarbon chain comprising one or more unsaturated bonds is used to indicate an alkyl chain as indicated above which comprises one or more double or triple bonds; for example, a —CH=CH— vinyl group, propenyl, butenyl, etc.

Aryl group Ar is used to indicate mono or bicyclic aromatic groups comprising 5 to 14 carbon atoms, such as for example benzene and naphthalene, and the corresponding heterocycles thereof, comprising one or more heteroatoms selected from among O, N and S, such as for example, furan, pyrrole, thiophen, imidazole, pyridine, benzothiophen, indole, quinoline.

In a preferred aspect of the invention, a preferred arylic group is the phenyl, while preferred heterocyclic groups are pyridine and quinoline.

Preferably, in the compounds of the present invention, the saturated C1-C8 alkyl group $R^1$ is the methylene group (—CH$_2$—), while the group $R^4$ is preferably selected from among methylene, ethylene, propylene.

Regarding the acyloxy group (—O—C(O)—$R^3$), this is preferably substituted by a phenyl group ($R^3$=phenyl) in turn substituted with an acyloxy group (—O—C(O)—$R^4$).

Preferably, the acyloxy group is in ortho position and it comprises a group $R^4$ represented by an ethylene or propylene group substituted by an amino group (—NH$^2$).

Even more preferably, the group $R^4$ described above is selected from among 1-aminoethyl, 2-aminoethyl and aminopropyl.

Regarding the group $R^2$, the latter is preferably a cyan group (—CN) or an amide group (—CONH$_2$).

In an even more preferred aspect, the present invention describes the compounds:

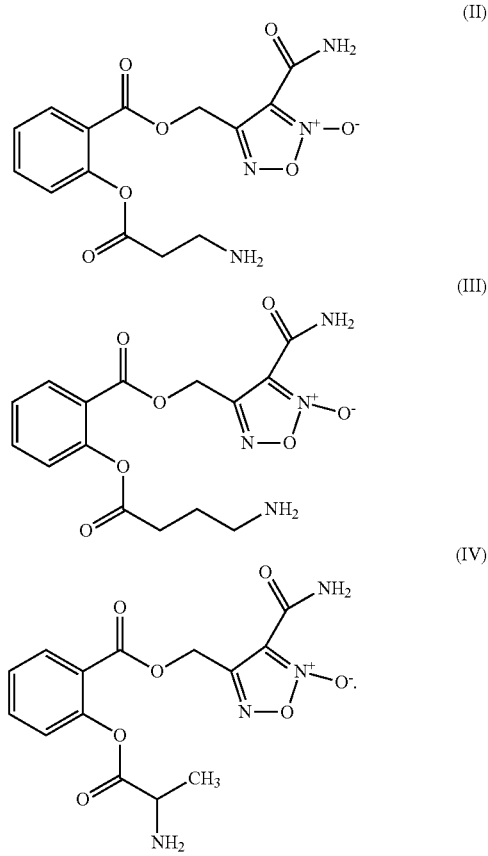

Pharmaceutically acceptable salts is used to indicate salts suitable for human or animal administration and having suitable technological properties, such as for example, sodium, potassium, ammonium, zinc salt or any salt with amino acids (see, for general reference, Remington's Pharmaceutical Sciences Handbook, Mack Pub. Co., N.Y., USA 17$^{th}$ edition, 1985).

The compounds of the invention advantageously showed to be particularly soluble in water and to be particularly stable in an acid environment at a 1-2 pH.

Instead, they have a short half-life ($t_{1/2}$<2 minutes) upon contact with human serum in that quickly hydrolyzed. Thus, the compounds of the invention are particularly suitable for use as medicine, in particular for the treatment of the pathologies correlated to the generation of reactive nitrogen species (RNS).

Examples of such pathologies comprise neoplasias, inflammatory diseases or chronic infections.

In a preferred aspect, the compounds of the present invention are used for the treatment of prostate cancer and, in particular, the compounds of formula (II), (III) and (IV), can be usefully used for such purpose.

Regarding this, the previously mentioned compounds can be formulated, together with suitable pharmaceutically acceptable excipients and additives according to the selected pharmaceutical form. In particular, one or more from among diluents, solvents, bulking agents, rheological modifiers, stabilisers, pH stabilisers, bonding agents, buffers, disaggregating agents, preservatives, elasticizing agents, emulsifiers, chelating agents, lubricating agents, edulcorants, sweetening agents, colouring agents and/or flavouring agents may be added.

As for the dosage of active ingredient, represented by a compound according the present invention, this may be determined according to the preselected pharmaceutical form and which can be defined by the pharmacology expert according to the required therapeutic protocol.

According to a further aspect, the described compounds can be used as adjuvants in the immunotherapy protocols against the pathologies correlated to the generation of reactive nitrogen species and, in particular, of the prostate cancer.

Such protocols comprise the administration of a pharmacologically efficient amount of compound to a patient, wherein said amount can be defined by the expert in immunotherapy treatment.

EXAMPLE 1

Preparation of ([3-(aminocarbonyl)furoxan-4-yl]methyl -2-(β-alanyloxy)benzoate)hydrochloride (compound MC526 (II))

The compound was prepared according to the scheme indicated in FIG. 1.

To a solution of [3-(aminocarbonyl)furoxan-4-yl]methyl salicylate (0.2 g; 0.716 mmols) and Boc-β-Ala-OH (0.17 g; 0.86 mmols) in $CH_2Cl_2$ (10 mL) there had been added DMAP cat and EDC.HCl (0.25 g; 0.86 mmols) and the mixture was stirred at ambient temperature for 2 hours.

After adding water, the solution was extracted with methylene chloride (3×10 ml). The organic phase was first washed with $NaHCO_3$ (2×20 ml), and then brine (10 ml), and it was then dried on anhydrous magnesium sulfate. The evaporation of the solvent at low pressure gave colourless oil which was purified by flash chromatography (PE/EtOAc 7/3 v/v eluent). The pure {[3-(aminocarbonyl)furoxan-4-yl]methyl 2-(3-[tert-butoxycarbonyl)amino]propanoyl}oxy)benzoate was thus obtained as colourless oil. The product was dissolved in 5 mL of a 2.36 M solution of hydrochloric acid in anhydrous dioxane and the resulting mixture was stirred at ambient temperature for two hours. The residue obtained after evaporating the solvent at low pressure was recovered with methylene chloride (3×15 ml) to obtain the desired product (II) with a yield of 80% in form of white solid.

The hydrochloride was recrystalised using absolute ethanol. Melting point: 102-104° C.

$^1$H-NMR (DMSO-$d_6$): δ 8.52 ($s_{br}$, 1H, —$CONH_2$); 8.19 ($s_{br}$, 2H, $NH_2$); 8.03-8.00 (m, 1H, Ph); 7.84 ($s_{br}$, 1H, —$CONH_2$); 7.79-7.74 (m, 1H, Ph); 7.47 (t, 1H, Ph); 7.37 (d, 1H, Ph); 5.60 (s, 2H, —$OCH_2$-Fx); 3.14-3.00 (m, 4H, 2-$CH_2$).

$^{13}$C-NMR (DMSO-$d_6$): δ 169.9; 163.9; 156.5; 155.4; 150.8; 135.8; 132.4; 111.3; 62.9; 58.7; 35.3; 32.4.

Anal. Calc. For $C_{14}H_{15}N_4O_7Cl×½H_2O$ C % 42.49. H % 4.07, N % 14.16; found C % 42.25, H % 3.88, N % 13.98.

EXAMPLE 2

Preparation of ([3-(aminocarbonyl)furoxan-4-yl]methyl-2-(4-amino butanoyloxy)benzoate hydrochloride) (compound MC596 (III))

Figure 2:
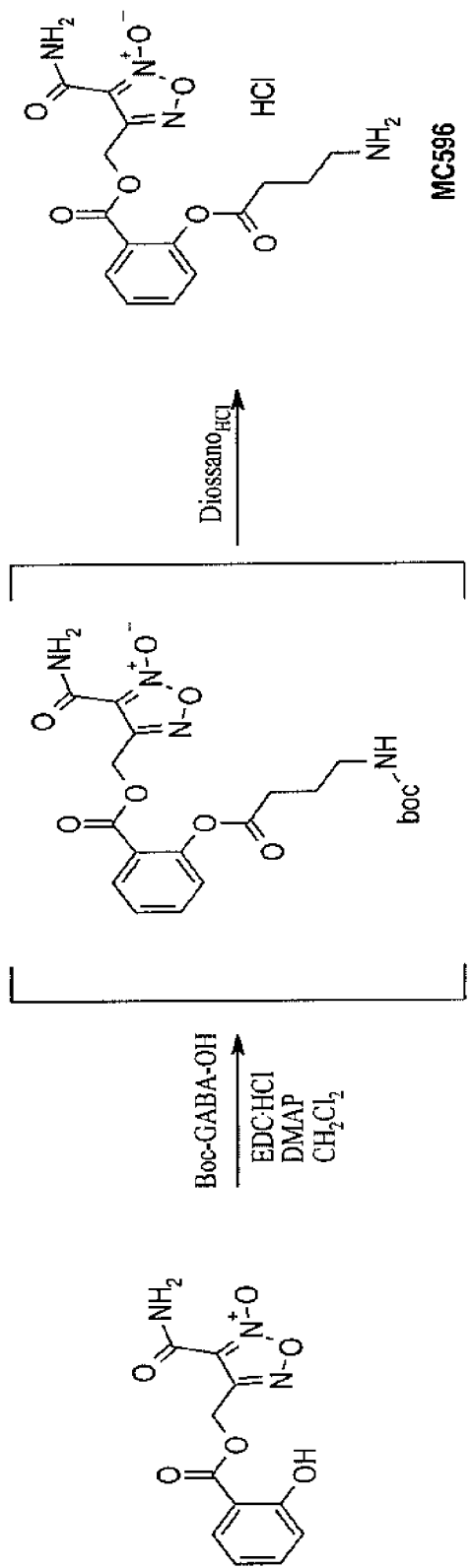
FIG. 2 represents the synthesis scheme of the compound MC596.
Figure 3:
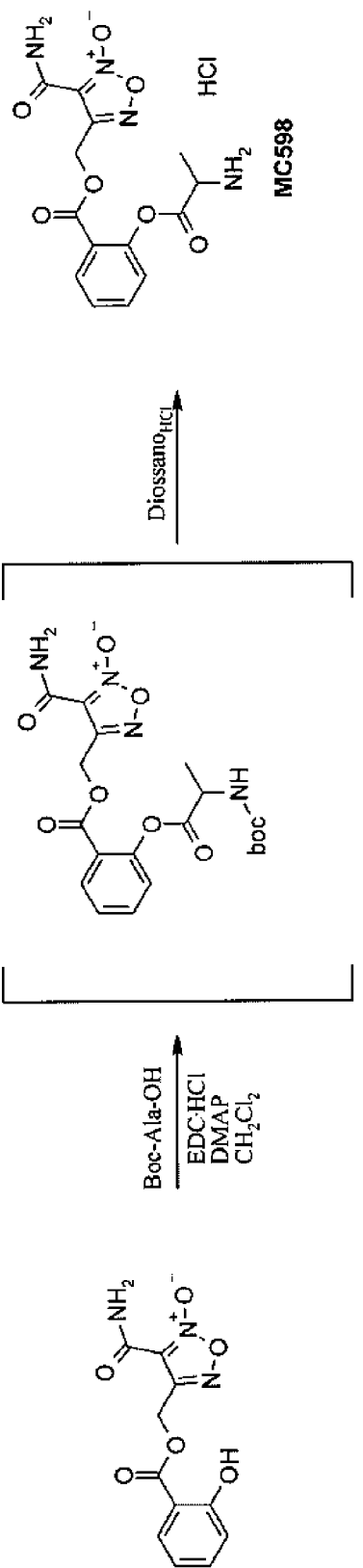
FIG. 3 represents the synthesis scheme of the compound MC598.

The compound was prepared according to the scheme indicated in FIG. 2.

In particular, to a solution of [3-(aminocarbonyl)furoxan-4-yl]methyl salicylate (0.28 g; 1.00 mmols) and Boc-GABA-OH (0.24 g; 1.20 mmols) in $CH_2Cl_2$ (20 mL) there were added MAP cat and EDC.HCl (0.36 g; 1.20 mmols) and the mixture was stirred at ambient temperature for 2 hours.

Then water was added and the solution was extracted with methylene chloride (3×10 ml); the organic phase was washed with $NaHCO_3$ (2×20 ml), brine (10 ml), dried with anhydrous magnesium sulfate and evaporated to give a colourless oil which was purified by flash chromatography eluting with PE/EtOAc 7/3 v/v to give {[3-(aminocarbonyl)furoxan-4-yl]methyl 2-(4-[tert-butoxycarbonyl)amino]butanoyl}oxy)benzoate as colourless oil.

The {[3-(aminocarbonyl)furoxan-4-yl]methyl 2-(3-[tert-butoxycarbonyl)amino]butanoyl}oxy)benzoate was dissolved in 5 mL of a 2.36 M solution of hydrochloric acid in anhydrous dioxane and the mixture was stirred at ambient temperature for two hours. Then the formed precipitate was filtered and the compound in question (III) was obtained with a yield of 70% in form of a white solid. The product was recrystalysed using absolute ethanol. Melting point: 190° C. with decomposition.

$^1$H-NMR (DMSO-$d_6$): δ 8.45 ($s_{br}$, 1H, —$CONH_2$); 8.09 ($s_{br}$, 2H, $NH_2$); 8.01-7.94 (m, 1H, Ph); 7.82-7.70 (m, 2H, Ph+—$CONH_2$); 7.44 (t, 1H, Ph); 7.30 (d, 1H, Ph); 5.58 (s, 2H, —$OCH_2$-Fx); 2.95-2.84 (m, 2H, —$CH_2NH_2$); 2.74 (t, 2H, —$CH_2CO$—); 1.95 (qi, 2H, —$CH_2CH_2$—).

$^{13}$C-NMR (DMSO-$d_6$): δ 170.9; 162.9; 155.5; 154.4; 150.1; 134.8; 131.4; 126.4; 124.2; 121.9; 110.3; 57.5; 37.8; 30.3; 22.0.

Anal. Calc. For $C_{15}H_{17}N_4O_7Cl$ C % 44.95, H % 4.28, N % 13.98; found C % 44.96, H % 4.28, N % 13.79.

EXAMPLE 3

Preparation of ([3-(aminocarbonyl)furoxan-4-yl]methyl-2-(alanyloxy)benzoate hydrochloride) (compound MC598 (III))

Figure 4:
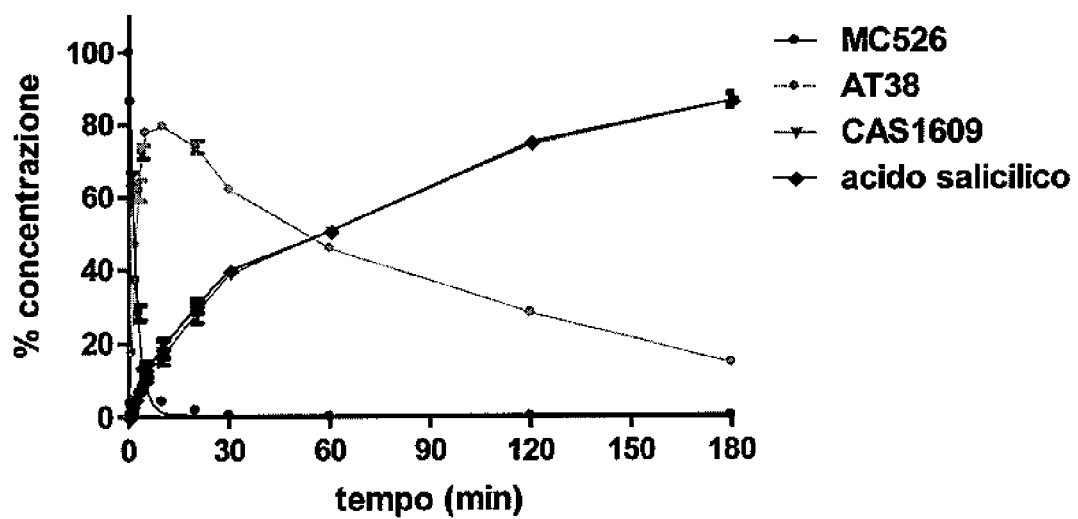
FIGS. 4, 5 and 6 show the results of the stability assay of the compounds MC526, MC596 and MC598, respectively, in human serum.

The compound was prepared according to the diagram indicated in FIG. 4.

In particular, to a solution of [3-(aminocarbonyl)furoxan-4-yl]methyl salicylate (0.28 g; 1.00 mmols) and Boc-Ala-OH (0.23 g; 1.20 mmols) in $CH_2Cl_2$ (20 mL) there were added DMAP cat and EDC.HCl (0.36 g; 1.20 mmols) and the mixture was stirred at ambient temperature for 2 hours.

Then water was added and the solution was extracted with methylene chloride (3×10 ml); the organic phase was washed with $NaHCO_3$ (2×20 ml), brine (10 ml), dried with anhydrous magnesium sulfate and evaporated to obtain a colourless oil which was purified by flash chromatography eluting with PE/EtOAc 7/3 v/v to give {[3-(aminocarbonyl)furoxan-4-yl]methyl 2-(2-[tert-butoxycarbonyl)amino]propanoyl}oxy)benzoate as colourless oil.

The {[3-(aminocarbonyl)furoxan-4-yl]methyl 2-(3-[tert-butoxycarbonyl)amino]propanoyl}oxy)benzoate was dissolved in 5 mL of a 2.36 M solution of hydrochloric acid in anhydrous dioxane and the mixture was stirred at ambient temperature for two hours. Then, the formed precipitate was filtered and the compound in question is obtained (IV) with a yield of 60% in form of a white solid.

The product was recrystalysed using absolute ethanol. Melting point: 185° C. with decomposition.

$^1$H-NMR (DMSO-$d_6$): δ 8.81 ($s_{br}$, 2H, —$NH_2$); 8.54 ($s_{br}$, 1H, —$CONH_2$); 8.05-8.02 (m, 1H, Ph); 7.85-7.78 (m, 2H,

Ph+—CONH$_2$); 7.55-7.49 (m, 1H, Ph); 7.41-7.39 (m, 1H, Ph); 5.61 (s, 2H, —OCH$_2$-Fx); 4.42-4.35 (m, 1H, —CH); 1.62 (d, 3H, —CH$_3$).

$^{13}$C-NMR (DMSO-d$_6$): δ 168.4; 162.7; 155.5; 154.4; 149.1; 135.0; 131.5; 127.1; 123.8; 121.8; 110.3; 62.7; 57.6; 15.4.

Anal. Calc. For C$_{14}$H$_{15}$N$_4$O$_7$Cl×0.25 H$_2$O C % 42.98, H % 3.99, N % 14.32; found C % 42.90, H % 3.99, N % 14.30.

EXAMPLE 4

Stability Studies

The stability of the compound MC526 was studied through reverse phase chromatography in an aqueous medium at pH=1 and in the human serum at 37° C.

In particular, a 10 mM solution of the compound of Example 1 in DMSO was added to a 0.1 M solution of HCl preheated to 37° C. The final concentration of the compound was 100 μM. The resulting solution was maintained at 37±0.5° C. and 20 μl aliquots of the reaction solution were analysed by means of RP-HPLC at suitable time intervals.

In order to assay the stability of the compound of Example 1 in human serum, a 10 mM solution of the compound in DMSO was added to human serum (obtained from human AB plasma, Sigma) preheated to 37° C. The final concentration of the compound was 200 μM. The resulting solution was incubated at 37±0.5° C. and 300 μL aliquots of the reaction mixture were collected and added to an equal amount of acetonitrile containing trifluoroacetic acid 0.1% at suitable time intervals for deproteinising the serum. The sample was sonicated, vortexed and then centrifuged for 10 minutes at 2150 g. The white supernatant was filtered using PTFE 0.45μm (Alltech) filters and analysed through RP-HPLC.

The analysis in RP-HPLC allows separating and quantifying the initial compounds and those deriving from hydrolysis. Analysis was carried out using a HP1100 (Agilent Technologies, Palo Alto, Calif., USA) chromatography system equipped with a quaternary pump (model G1311A), a degassing membrane (G1379A), a diode-array detector (DAD) (model G1315B) integrated in the HP1100 system. A HP ChemStation (Agilent Technologies) system was used for analyzing data. The analytic column was Nucleosil 100-5 C18 Nautilus (250×4, 6 mm, size of the particles 5 μm) (Macherey-Nagel). The mobile phase used was constituted by acetonitrile/water (55/45) with 0.1% trifluoroacetic acid and the flow rate is of 1.2 ml/min. The injection volume was 20 μl (Rheodyne, Cotati, Calif.). The effluent from column was monitored at 226 nm (for the compound MC526 and for CAS 1609) and at 240 nm (for salicylic acid and the salicylate AT38 against a reference at 600 nm. The quantification of the initial products and those deriving from hydrolysis was carried out by means of calibration curves obtained using standards studied in the same conditions (for concentrations comprised between 5 and 200 μM).

The compounds revealed to be moderately stable at pH=1 (more than 60% of the compound was unaltered after 1 hour of incubation).

The results of the assays are indicated in the following table.

| COMPOUND | Stability in buffer at pH = 1 after 1 hour |
|---|---|
| MC526 | 60% |
| MC596 | 90% |
| MC598 | 80% |

When incubated in human serum, the compounds hydrolyse quickly (t$_{1/2}$<2 minutes) into the salicylate derivative (AT38) which slowly releases the CAS 1609 compound and salicylic acid according to the scheme below which reports the hydrolysis of the compound MC526.

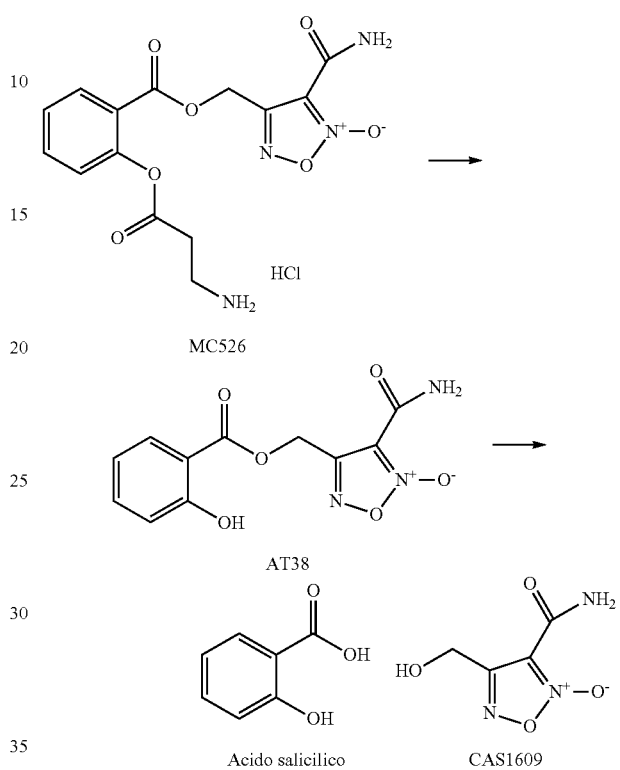

Figure 5:
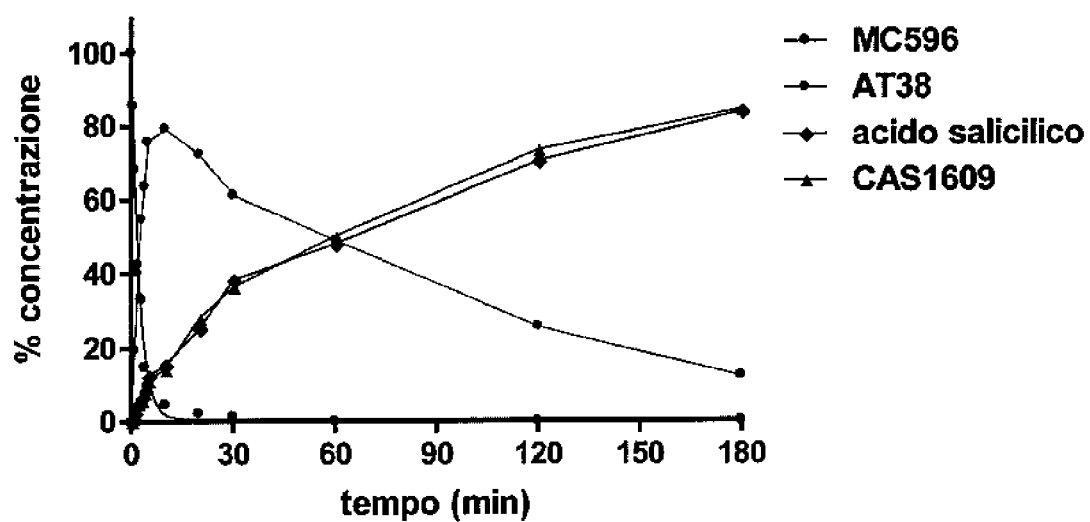
Figure 6:
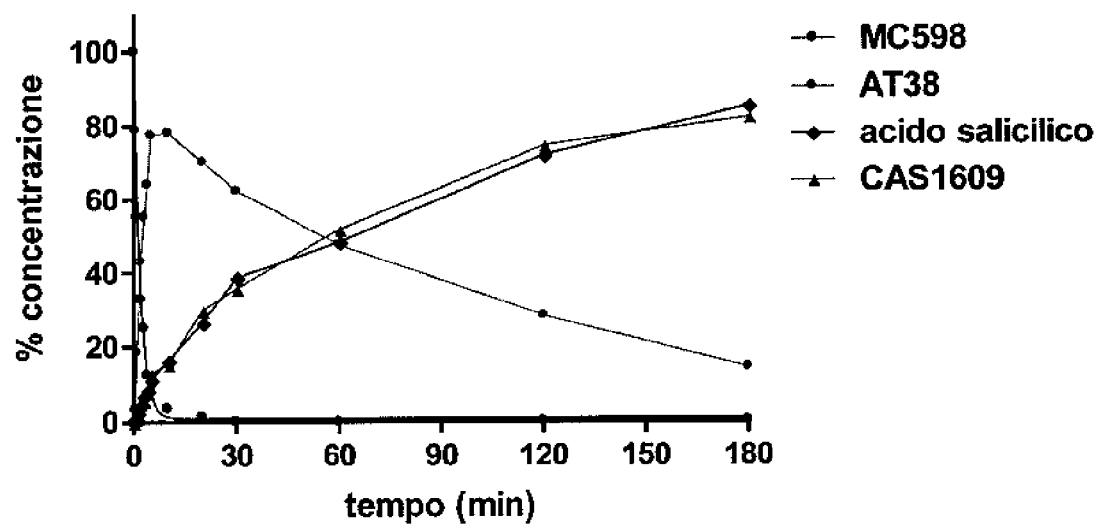

The results of the stability assay in human serum are indicated in the table below and in FIGS. 4, 5 and 6.

| COMPOUND | Stability in human serum t$_{1/2}$ (min) |
|---|---|
| MC526 | 1.4 |
| MC596 | 1.6 |
| MC598 | 1.3 |

EXAMPLE 5

Solubility

The table below shows the data regarding the solubility of the compounds of the invention and of a reference compound (AT38).

| COMPOUND | Solubility in water |
|---|---|
|  AT38 | <1 mg/L |

-continued

| COMPOUND | Solubility in water |
|---|---|
| MC526 | 10 g/L |
| MC596 | 2.5 g/L |
| MC598 | 10 g/L |

Materials and Methods

Cell Lines and Mice

CT26 (H-2d), a colon carcinoma induced in BALB/c; MBL-2 (H-2b), with Moloney virus induced lymphoma; C26-GM, a cell line derived from the colon carcinoma C26 (H-2d) genetically modified for releasing a granulocytes-macrophages stimulating factor (GM-CSF).

The cells are grown in DMES (Invitrogen) or in RPMI 160 (Euroclone) supplemented with 2 mM L-glutamine, 10 mM HEPES (DMEM) or 1 mM piruvate sodium (RPMI 1640), 20 mM 2-mercaptoethanol, 150 units/ml streptomycin and 200 units/ml of penicillin, 10% heat inactivated FBS (Invitrogen or BioWhittaker).

The mice BALB/c (H-2d) and C57BL/6 (H-2d) (eight weeks old) were acquired from HArlan.

The mice BALB/c were inoculated s.c. in the inguinal cavity with $0.5*10^6$ cells C26GM. The mice were sacrificed after 9 days and the splenocytes were used for in vitro assays.

For in vivo experiments, the mice BALB/c were inoculated $0.5*10^6$ cells C26GM sub-cutaneous in the on the left side.

Proliferation Assay

The splenocytes of the BALB/C from the control animal group and from the animals carrying colon carcinoma26 (C26GM) are plated to the concentration of $6*10^5$ cells per well and stimulated with 3 μg/ml anti-CD3 (2C11, ATCC) and 2 μg/ml of anti-CD28 (clone 37.5, ATCC) both with and without scalar dilutions of the compounds subject of the invention. After 3 days of incubation, 1 μCi/well (1 Cl=37 GBq) of $^3$H-TdR (PerkinElmer) is added to the culture for 18 hours and the addition thereof is monitored by scintillation.

Figure 7:
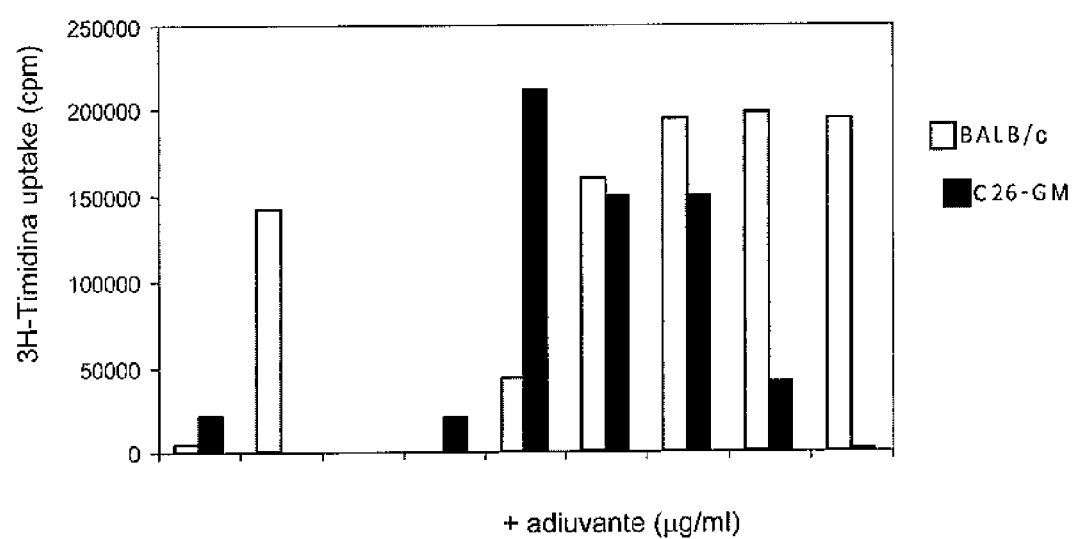
FIG. 7 shows the results of the proliferation assay of the compound MC526.

FIG. 7 shows the results obtained by the proliferation assay. In particular, the controls (Unst) refer to cells not stimulated with antiCD3 and antiCD28 and the control (St) on stimulated cells but drug-free. It can be observed that the doses corresponding to 200 μM and 100 μM are toxic for the cells, in that the proliferation is not observed even on healthy splenocytes. The 50 μM dose is partly toxic on the healthy cells, but it allows recovering from suppression on splenocytes of mice with tumour. The 25 μM and 12.5 μM dosages are instead efficient and non-toxic.

Chromium Release Assay

Two different cell cultures were prepared to evaluate the CTL response. For the first, the BALB/c ($6*10^5$ cells per well) splenocytes are stimulated with ($6*10^5$ cells per well) of γ-radiated C57BL/6 splenocytes in 96-wells, flat plates (BD Falcon), both with and without the derivatives of the invention with scalar dilutions. In order to attain immunosuppressions, CD11b$^+$ cells from the spleen of tumour-carrying mice are added up to the final concentration of 3% to a mixture of lucocytes culture. In the second, the immunosuppressed splenocytes ($6*10^5$ cells per well) derived from the tumour-carrying mice are stimulated with ($6*10^5$ cells per well) of γ-radiated C57BL/6 splenocytes in 96-wells, flat plates (BD Falcon), both with and without the derivatives of the invention with scalar dilution. The percentage of CD11b$^+$ cells present in the spleen of these mice varies from 20 to 40%.

In both experimental conditions, after 5 days of incubation, the cultures were assayed to verify the ability to eliminate $2*10^3$ allogeneic (MBL-2) or syngenic target cells in the $^{51}$Cr release assay in 5 hours.

The percentage of +specific lysis was calculated from triplicate samples as follows: (experimental cpm−spontaneous cpm)/(maximum cpm-spontaneous cpm)*100, wherein 30 lytic units (LU30) represent the number of CTL cells that eliminate 30% of the target cells.

Figure 8A:
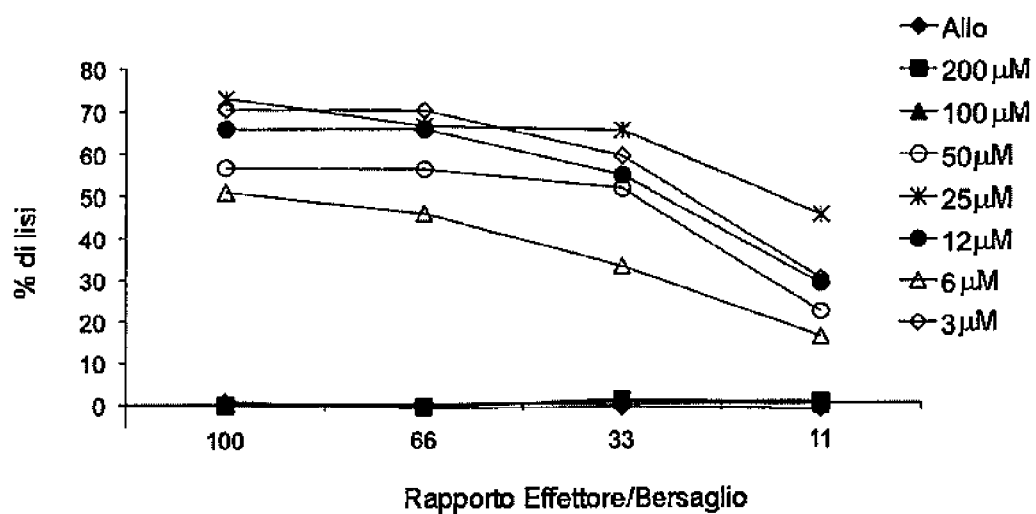
FIG. 8 shows the results of the chromium release assay.
Figure 8B:
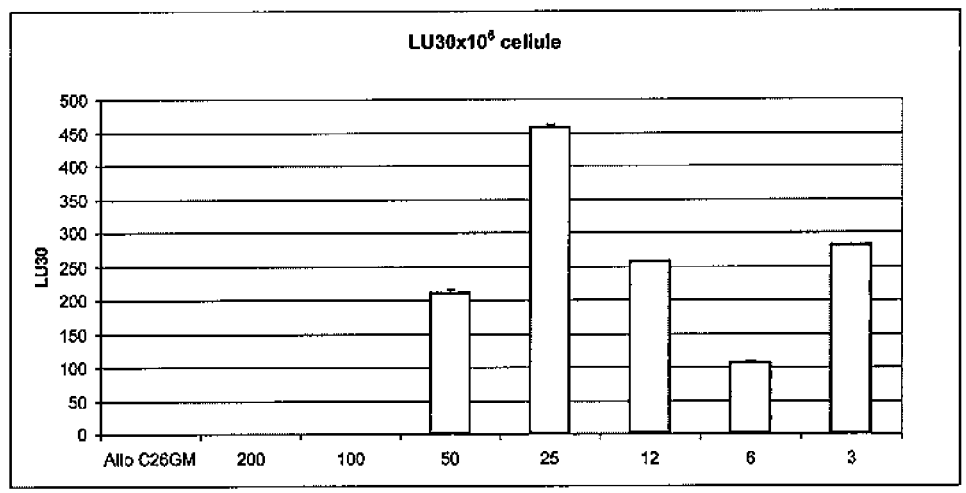

In FIG. 8A, Allo indicates the control of the reaction and it is equivalent to zero, in that the reaction is conducted in an immunosuppressed environment. The curve represents the percentage of lysis in 4 different serial dilutions (100, 66, 33, 11) of effectors (activated lymphocytes). As observable, the 200 μM and 100 μM dosages are toxic given the absence of recovery of cytotoxic function by the lymphocytes. With lower dosages with efficiency reducing there is a recovery activity comparable to the conditions of the response from healthy splenocytes. FIG. 8B shows the results in lytic units (LU).

Immunohistochemistry

The tumours are fixated in PLP fixative (periodate-lysine-paraformaldehyde), cryoprotected in 30% sucrose and frozen in OCT. The samples are cut with a cryostat (6 mm) and after air drying, the sections are fixated with acetone for 3 minutes. Subsequently, the sections are rehydrated with PBS and endogenous peroxidase activity and the specific sites are blocked. The tissue sections are incubated with anti-nitrotyrosine (a:200, Calbiochem) or anti-CD3 (1:50, Dako) primary antibodies for 2 hours at ambient temperature. After washings with PBS, the samples are incubated with secondary antibodies conjugated to the peroxidase (Dako) for 1 hour at ambient temperature. The immunoreactivity is displayed with 3,3-diaminobenzidine (DAB). The sections are counterpigmented with hematoxylin and mounted in Eukitt.

Cytotoxicity Assay

The cytotoxicity assay is carried out to evaluate the efficiency of the compounds of the invention at restoring the cytolitic activity of the cells T against the allogeneic target cells using two different immunosuppressive conditions.

The invention claimed is:

1. A compound having a formula selected from the group consisting of:

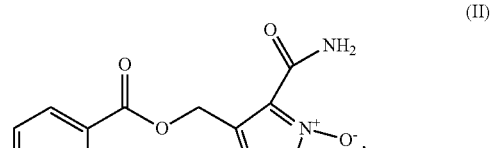

(II)

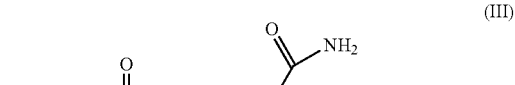

(III)

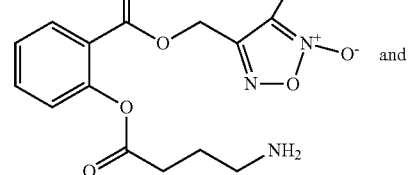

and

-continued

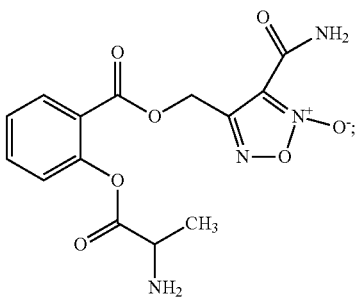

(IV)

and pharmaceutically acceptable salts thereof.

2. A method for the treatment of a pathology characterised by the generation of reactive nitrogen species, comprising the step of administering to a patient in need thereof of a pharmacologically effective amount of the compound of claim 1.

3. The method of claim 2, wherein said pathology is selected from the group consisting of neoplasia, inflammatory disease and chronic infection.

4. The method of claim 3, wherein said pathology is prostate cancer.

5. A method for stimulating the immune response against neoplastic cells comprising administering to a subject in need thereof a pharmacologically effective amount of the compound of claim 1.

6. The method of claim 5, wherein the neoplastic cells are associated with prostate cancer.

7. A pharmaceutical composition comprising the compound of claim 1.

8. The pharmaceutical composition of claim 7 comprising pharmaceutically acceptable excipients and additives selected from the group consisting of:

diluents, solvents, bulking agents, rheological modifiers, stabilisers, pH stabilisers, bonding agents, buffers, disaggregating agents, preservatives, elasticizing agents, emulsifiers, chelating agents, lubricating agents, edulcorants, sweetening agents, colouring agents and flavouring agents, alone or in any combination thereof.

* * * * *